United States Patent [19]

Ohorodnik et al.

[11] 4,209,460
[45] Jun. 24, 1980

[54] PRODUCTION OF PURE ACETYL CHLORIDE

[75] Inventors: Alexander Ohorodnik; Eberhard Auer; Klaus Gehrmann, all of Erftstadt, Fed. Rep. of Germany

[73] Assignee: Hoechst Aktiengesellschaft, Fed. Rep. of Germany

[21] Appl. No.: 974,069

[22] Filed: Dec. 28, 1978

[30] Foreign Application Priority Data

Dec. 29, 1977 [DE] Fed. Rep. of Germany ....... 2758682

[51] Int. Cl.$^2$ ..................... C07C 51/58; C07C 51/42
[52] U.S. Cl. ................................................. 260/544 Y
[58] Field of Search ................................... 260/544 Y

[56] References Cited

U.S. PATENT DOCUMENTS

| | | | |
|---|---|---|---|
| 1,359,071 | 11/1920 | Kaufmann | 260/544 Y |
| 1,936,739 | 11/1933 | Townend | 260/544 Y |
| 3,636,102 | 1/1972 | Lippman | 260/544 Y |
| 3,959,360 | 5/1976 | Vazopolos | 260/544 Y |

FOREIGN PATENT DOCUMENTS 642519  3/1937  Fed. Rep. of Germany ...... 260/544 Y

*Primary Examiner*—Paul Killos
*Attorney, Agent, or Firm*—Connolly and Hutz

[57] ABSTRACT

Pure acetyl chloride containing less than 1 ppm of phosphorus is produced. To this end, crude acetyl chloride containing phosphorus compounds is intimately contacted with 1 to 20 liters of gaseous chlorine per liter of liquid crude acetyl chloride and the acetyl chloride so contacted with chlorine is subjected to fractional distillation.

2 Claims, No Drawings

PRODUCTION OF PURE ACETYL CHLORIDE

This invention relates to the production of acetyl chloride.

Acetyl chloride is a reagent of which price and purity critically influence its widespread used in chemistry. Commercial grade acetyl chloride normally has a purity of about 98%. For a variety of typical uses, it is however necessary to employ acetyl chloride with a purity of at least 99%.

The production of 2,5-dioxo-1-oxa-2-phospholanes from dichlorophosphanes, acrylic acid and acetic anhydride is always accompanied by the formation of considerable quantities of contaminated acetyl chloride which, for reasons of environmental protection and economy, cannot simply be destroyed by hydrolysis and neutralization or by incineration. It is therefore highly desirable to have a process permitting contaminated acetyl chloride to be transformed to pure and widely applicable acetyl chloride.

Depending on its origin, acetyl chloride may contain up to about 20 weight % of contaminants, from which it can be freed in known manner, e.g. by fractional distillation. It cannot however satisfactorily be freed in the manner described from chemically combined phosphorus which may be present in acetyl chloride in varying proportions up to 1000 ppm (ppm stands for part per million). In various fields, it is however desirable and even necessary to have acetyl chloride containing not more than 1 ppm of phosphorus. Needless to say, therefore, it is highly desirable to have a process for purifying acetyl chloride and reducing its phosphorus content to less than 1 ppm.

Analytical investigations have shown the phosphorus content to originate from phosphorus trichloride. This is a contaminant contained in dichlorophosphane which is used as one of the starting materials for making 2,5-dioxo-1-oxa-2-phospholanes. Further investigations have shown that acetyl chloride (bp=50.9° C.) cannot be freed distillatively from minor proportions of PCl$_3$ (bp=75.9° C.).

In the concentration range concerned, the PCl$_3$/acetyl chloride system presents boiling and dew curves which are very close to each other. In other words, it would be necessary to employ a column with an unreasonably high number of trays for the separation of the system into its components.

The present invention now unexpectedly provides a process for purifying contaminated acetyl chloride by first subjecting it to treatment with chlorine and then to fractional distillation. During the chlorination, PCl$_3$ undergoes conversion to PCl$_5$ which in admixture with acetyl chloride shows a normal boiling behaviour (sublimation point=159° C.).

Acetyl chloride which is so purified has a purity of more than 99% and contains less than 1 ppm of phosphorus.

The present invention relates more particularly to a process for making pure acetyl chloride containing less than 1 ppm of phosphorus, which comprises: intimately contacting crude acetyl chloride containing phosphorus compounds with 1 to 20, preferably 10 to 15, liters of gaseous chlorine per liter of liquid crude acetyl chloride and subjecting the acetyl chloride so contacted with chlorine to fractional distillation.

The following Examples illustrate the invention which is not limited thereto.

EXAMPLE 1 (Comparative Example)

A distilling apparatus comprised of a circulation evaporator with a capacity of 2.5 liters, a column 2 meters long, 50 mm wide and filled with 8 mm saddle-shaped packing material, and a cooler with a reflux distributing means was fed, per hour, with 2.8 l of crude acetyl chloride composed as follows (in weight %):

Acetyl chloride—85.97
Acetic acid—0.52
Acrylic acid chloride—4.94
Vinylidene chloride (CH$_2$=CCL$_2$)—0.12
Acetic anhydride—7.60
Mixed acetic/acrylic anhydride—0.86
P-content—125 ppm The circulation evaporator was operated at 82° to 83° C. under a reflux ration of 1:1 and 2.32 l/h of pure acetyl chloride was obtained overhead. It was composed as follows (in weight %):

Acetyl chloride—99.32
Acrylic acid chloride—0.52
Acetic anhydride—0.15
P-content—9 ppm 475 ml of base product was taken per hour from the circulation evaporator. The experiment was carried out over a period of 24 hours.

EXAMPLE 2

A tubular structure 100 mm wide and 120 cm long, which was placed in an upright position and filled with coarse saddle-shaped packing material was fed from above with 2.4 l/h of acetyl chloride, which had the composition indicated in Example 1, and 29–30 l/h of chlorine gas was admitted from below. By means of a riser, the chlorine-containing acetyl chloride was taken from the tubular structure and delivered to the distilling apparatus described in Example 1. The circulation evaporator was operated at 83° to 84° C. under a reflux ratio of 1:1 and 1.96 l/h of pure acetyl chloride was obtained. It was composed as follows (in weight %):

Acetyl chloride—99.78
Acetic anhydride—0.22
P-content—less than 1 ppm

The experiment was carried out over a period of 36 hours. Altogether 15.5 l of base product was taken from the circulation evaporator.

EXAMPLE 3

The apparatus was the same as that used in Example 2. 2.2 l/h of crude acetyl chloride with the following composition (in weight %):

Acetyl chloride—86.31
Acetic acid—0.59
Acrylic acid chloride—4.94
Vinylidene chloride—0.06
Acetic anhydride—7.15
Mixed acrylic/acetic anhydride—0.95
P-content—26 ppm was treated in the apparatus with 25–26 l/h of chlorine and distilled in the distilling apparatus described. The circulation evaporator was operated at 83° to 84° C. under a reflux ratio of 1:1 and 1.8 l/h of pure acetyl chloride was obtained. The experiment was stopped after 204 hours and a specimen of distillate, which was collected, was analyzed. It was composed as follows (in weight %):

Acetyl chloride—99.56
Acrylic acid chloride—0.21

Acetic anhydride—0.23
P-content—less than 1 ppm

Altogether 81 l of base product was taken from the circulation evaporator during the experiment.

We claim:

1. A process for making pure acetyl chloride containing less than 1 ppm of phosphorus which comprises: intimately contacting crude acetyl chloride having been recovered as a by-product in the production of 2,5-dioxo-1-oxa-2-phospholanes from dichlorophosphanes, acrylic acid and acetic anhydride and containing phosphorus compounds with 1 to 20 liters of gaseous chlorine per liter of liquid crude acetyl chloride and subjecting the acetyl chloride so contacted with chlorine to fractional distillation.

2. A process as claimed in claim 1, wherein 10 to 15 liters of chlorine is used per liter of acetyl chloride.